(12) United States Patent
Moulder

(10) Patent No.: US 8,812,092 B2
(45) Date of Patent: Aug. 19, 2014

(54) ORIENTATION DETERMINATION FOR AN IMPLANTABLE MEDICAL DEVICE

(75) Inventor: J. Christopher Moulder, Portland, OR (US)

(73) Assignee: Biotronik CRM Patent AG (CH)

( * ) Notice: Subject to any disclaimer, the term of this patent is extended or adjusted under 35 U.S.C. 154(b) by 712 days.

(21) Appl. No.: 12/902,913

(22) Filed: Oct. 12, 2010

(65) Prior Publication Data

US 2011/0087114 A1 Apr. 14, 2011

Related U.S. Application Data

(60) Provisional application No. 61/251,328, filed on Oct. 14, 2009.

(51) Int. Cl.
*A61B 5/04* (2006.01)

(52) U.S. Cl.
USPC .......................................... 600/512

(58) Field of Classification Search
USPC .......................................... 600/512
See application file for complete search history.

(56) References Cited

U.S. PATENT DOCUMENTS

| 7,899,520 B2 | 3/2011 | Lian et al. |
| 2003/0023175 A1 | 1/2003 | Arzbaecher |
| 2003/0083587 A1 | 5/2003 | Ferek-Petric |
| 2007/0276445 A1 * | 11/2007 | Sanghera et al. ............... 607/28 |

FOREIGN PATENT DOCUMENTS

| EP | 1 995 685 A2 | 11/2008 |
| WO | WO 2006/039693 A1 | 4/2006 |

OTHER PUBLICATIONS

European Search Report, EP 10 17 7974, Mar. 4, 2011.

* cited by examiner

*Primary Examiner* — Eric D. Bertram

(74) *Attorney, Agent, or Firm* — Craig A. Fieschko, Esq.; DeWitt Ross & Stevens S.C.

(57) ABSTRACT

An implantable medical device (IMD) is provided which is capable of sensing and determining its orientation, and of determining whether the IMD has been displaced over time away from its original or optimal position. Electronic components of the IMD, including a processor, digital memory, signal conditioning components, and a power supply, are preferably hermetically sealed within a biocompatible housing. At least three subcutaneous electrodes have fixed relative spacing for sensing electrical cardiac activity for various combinations of two electrodes, forming sensing vectors. Amplitude ratios and sign indicators associated with the sensing vectors are compared with a reference to determine an orientation of the device. In one embodiment, a telemetry unit transmits orientation data as a function of time to a remote device, and the remote device compares different stored orientations to detect displacement over time.

20 Claims, 10 Drawing Sheets

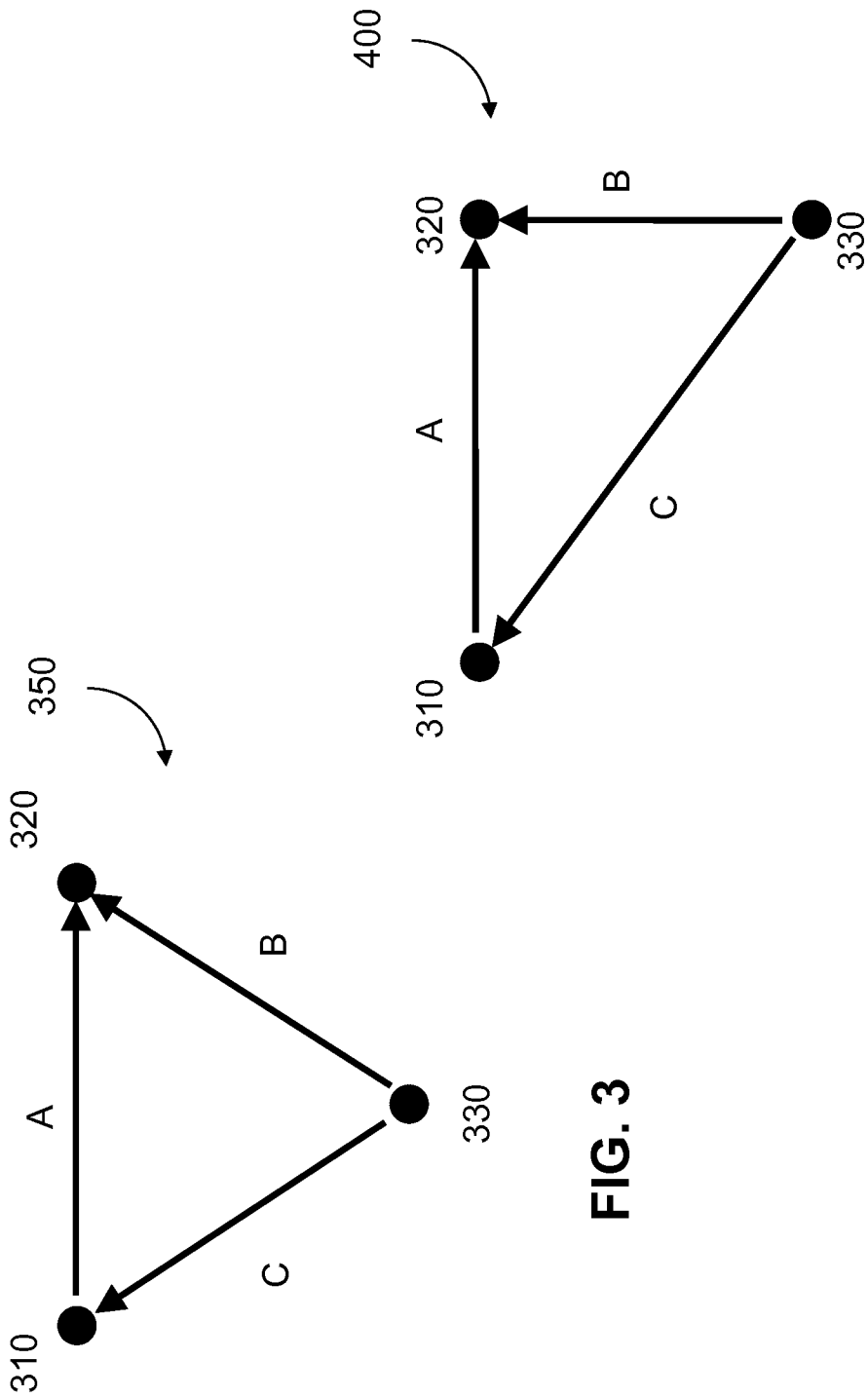

ORIENTATION DETERMINATION FOR AN IMPLANTABLE MEDICAL DEVICE

RELATED APPLICATION

This patent application claims the benefit of U.S. Provisional Patent Application No. 61/251,328 filed on Oct. 14, 2009, which is hereby incorporated by reference in its entirety.

TECHNICAL FIELD

The present disclosure relates to implantable medical devices and, in particular, to subcutaneous implantable medical devices capable of detecting electrical signals from the heart for monitoring heart activity.

BACKGROUND

An electrocardiogram (ECG) is well known in the art as a transthoracic interpretation of electrical activity of the heart as detected by electrodes. Electrical impulses in the heart originate in the sinoatrial node and travel through an intrinsic conducting system to the heart muscle. The impulses stimulate myocardial muscle fibers to contract and thus induce systole. These electrical impulses may be detected by a set of three electrodes (electrical contacts) selectively placed on the skin. An ECG represents a voltage measured between pairs of these electrodes and the muscle activity that the electrodes detect from different directions, or vectors. A typical shape of the systolic portion of an ECG output signal, plotted as a time-varying voltage, is known to those skilled in the art as the "QRS complex" in which Q, R, and S designate typical feature shapes that correspond to events in a cardiac cycle.

Present day implantable cardiac devices such as pacemakers, implantable defibrillators, and the like, include a monitoring function that may use either intracardiac or subcutaneous electrodes to sense electrical signals from the heart, in a similar fashion to a conventional, external ECG. Intracardiac electrodes are implanted directly into the heart tissue; whereas subcutaneous electrodes are fixedly attached to the housing of the implantable device. If subcutaneous electrodes are used, the resultant recording is called a subcutaneous electrocardiogram (SECG). Existing subcutaneous monitoring devices typically use only two electrodes (one pair), thus providing only one recording channel. Because the separation between the electrodes is small (due to the device size), the distance to the heart is relatively large, and skeletal muscle is in close proximity to the device, signals detected by subcutaneous electrodes are more susceptible to noise than are signals detected by implanted leads placed directly on the heart tissue. Signals detected by subcutaneous electrodes are also highly dependent upon orientation of the monitoring device with respect to the heart. Proper placement of the monitoring device is required during implantation to ensure optimal signal amplitude. The implanted device is preferably positioned so as to maximize the QRS signal amplitudes detected.

After implantation, it is generally difficult to identify movement of the device away from its optimal position. Such a displacement may cause a decrease in electrocardiographic signal amplitudes, resulting in a poor quality SECG. If such a decrease in signal strength occurs, existing devices generally cannot distinguish whether or not the reason is due to a shift in the device position. To confirm the orientation of the device, inspection by a physician currently requires the patient to travel to the physician and possibly to receive an X-ray. For at least these reasons, an improved method of determining the orientation of implantable heart monitoring devices is needed.

SUMMARY

An implantable medical device (IMD) is provided which is capable of a) sensing and self-determining its orientation, and b) determining whether the IMD has been displaced over time away from its original position. Electronic components within the IMD, including a processor, a digital memory, a power supply, signal conditioning components, and a telemetry unit, are preferably hermetically sealed within a biocompatible housing. A preferred embodiment of the device applies to monitoring for the purpose of assessing cardiac function. At least three subcutaneous electrodes are deployed for sensing electrical cardiac activity between pairs of electrodes, forming a set of at least three sensing vectors, thus providing three recording channels, each channel having one electrode in common with at least one other channel. Because subcutaneous electrodes are attached to a rigid device housing, their relative spacing is fixed as opposed to intracardiac electrodes which move as the heart expands and contracts, and skin electrodes, which also may be independently affected by different bodily motions. Amplitude ratios and sign indicators characterizing the sensing vectors are compared against a reference to determine an orientation of the IMD. In one embodiment, a telemetry unit transmits orientation data as a function of time to a remote device, and the remote device compares the orientation data against one or more stored orientations to detect displacement of the implanted device over time.

DESCRIPTION OF THE DRAWINGS

The present invention will now be explained in greater detail on the basis of exemplary embodiments with reference to the figures. In the Figures

FIG. 3 is a diagram of a preferred configuration for subcutaneous electrode placement in which three sensing vectors form an isosceles triangle.

FIG. 4 is a diagram of an alternative configuration for subcutaneous electrode placement in which three sensing vectors form a right triangle.

DETAILED DESCRIPTION

Figure 1:
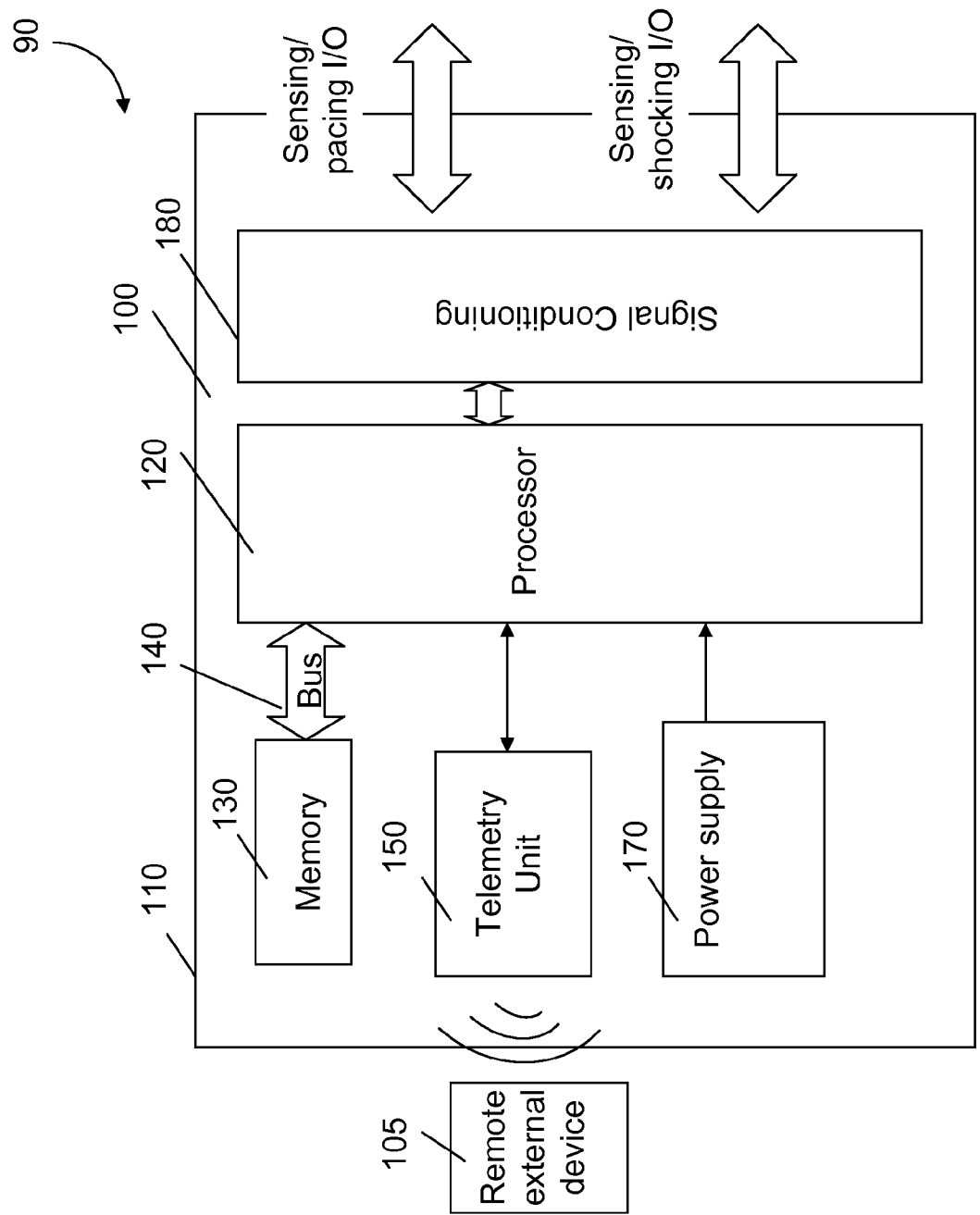
FIG. 1 is a block diagram of an exemplary prior art implantable medical device (IMD) system that includes a telemetry unit for communicating with a remote device.

With reference to FIG. 1, an implantable medical device (IMD) system 90 includes an IMD 100 in communication with a remote external device 105. IMD 100, having the disclosed features, may include existing cardiac monitoring device hardware such as, for example, an implantable loop recorder, a leadless pacemaker, or a leadless defibrillator. Such devices are well known in the art. The following embodiments describe features required in addition to features known in the art to carry out the present invention. As shown in FIG. 1, electronic components of IMD 100 are preferably surgically deployed within a hermetically sealed, biocompatible housing 110 that protects the components and minimizes reactions between the device and the surrounding living tissue. Electronic components within housing 110 include a processor 120 coupled to a digital memory 130 via a bus 140; a telemetry unit 150 coupled to processor 120; and a power supply 170, typically in the form of a battery, for energizing processor 120, digital memory 130, and telemetry unit 150. A suitable processor 120 may take the form of a Motorola 68000 series, Intel 8086, or similar 8-bit microprocessor, a programmable microcontroller, or another similar logic device typically implemented in IMDs. A suitable low power digital memory has the capacity to store SECG data.

Processor 120 is further coupled to a set of signal conditioning components 180. Signal conditioning components 180 may comprise, for example, one or more of a sense amplifier, a filter, and an analog-to-digital converter that samples input signals using a predetermined sampling rate. Suitable signal conditioning components known in the art, include signal conditioning components implemented in implantable loop recorders, pacemakers or defibrillators.

Telemetry unit 150 enables wireless communication with remote device 105 of data recorded by signal conditioning components 180 or stored in the digital memory 130. Telemetry unit 150 may be further wired, or wirelessly connected, to a remote server, expert center, or database. A suitable telemetry unit 150 known in the art may be inductive or radio frequency (RF) based.

Figure 2:
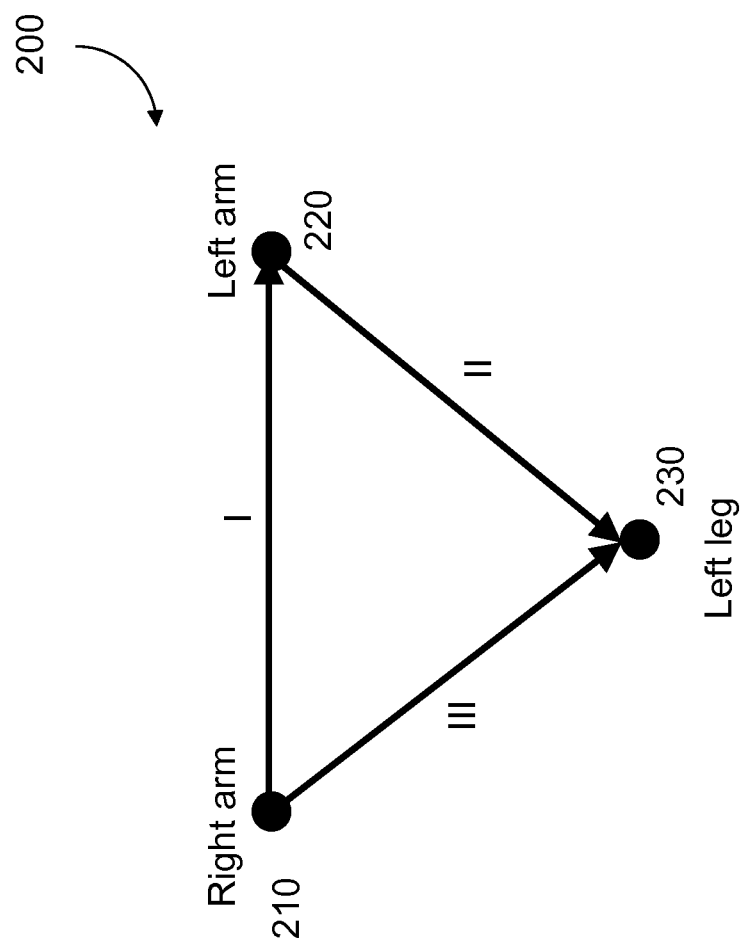
FIG. 2 is a diagram of Einthoven's triangle, showing a typical prior art configuration for placing external electrodes on the skin to sense electrocardiographic (ECG) signals.

Referring now to FIG. 2, electrodes used for obtaining conventional, surface ECG measurements are typically arranged in a triangle 200, known to those skilled in the art as Einthoven's triangle, such that a first electrode 210 is placed on, or in the direction of the right arm, a second electrode 220 is placed on, or in the direction of the left arm, and a third electrode 230 is placed on or in the direction of the left leg. Signals measured by leads I, II, and III, extending between pairs of electrodes, are understood as vectors, wherein the amplitude of the vector is the voltage between the pair of electrodes and the direction (theta) of the vector is determined by the arrangement of the electrode pairs. By convention, when electrode 220 is at a positive electric potential with respect to electrode 210, lead I is positive; when electrode 230 is at a positive electric potential with respect to electrode 220, lead II is positive; and when electrode 230 is at a positive electric potential with respect to electrode 210, lead III is positive;

Referring to FIGS. 3 and 4, IMD system 90 further includes three subcutaneous electrodes 310-330 that may be placed at, on, or in one end of housing 110, in a triangular configuration similar to Einthoven's triangle 200, for detecting electrical cardiac signals in a similar manner to skin electrodes 210-230 used in the exemplary external electrocardiogram (ECG) shown in FIG. 2. Signal conditioning components 180 coupled to electrodes 310-330 produce signals A, B, and C, for which three pairs of electrodes provide three SECG recording channels: a signal detected between electrodes 310 and 320 is measured as vector A; a signal detected between electrodes 330 and 310 is measured as vector B; and a signal detected between electrodes 330 and 320 is measured as vector C. Processor 120 is programmed to detect the QRS complex in sensing vectors A, B, or C and may provide the amplitude of the sensed vector signals at the point in time at which the QRS complex occurs. Or, processor 120 may combine sensing vectors A, B, or C, and may detect the QRS complex in the combined signal.

It is understood that the processing of sensing vectors A, B, and C is performed in a similar fashion as is known for some existing IMDs, in which signals are detected by bipolar electrodes implanted directly into the heart tissue. In particular, it is understood that signals A, B, and C are processed simultaneously, and that the sensed signal amplitudes may be stored in digital memory 130. FIGS. 3 and 4 show representations of two possible electrode placements: a preferred embodiment uses an isosceles triangular electrode configuration 350 for which vector orientations are shown in FIG. 3; an alternative embodiment uses a right triangular electrode configuration 400, for which two (A and B) of the three sensing vectors are orthogonal to each other as shown in FIG. 4. Thus, IMD 100 records an SECG of cardiac electrical activity in essentially the same fashion as described for a conventional ECG.

Figures 5, 6:
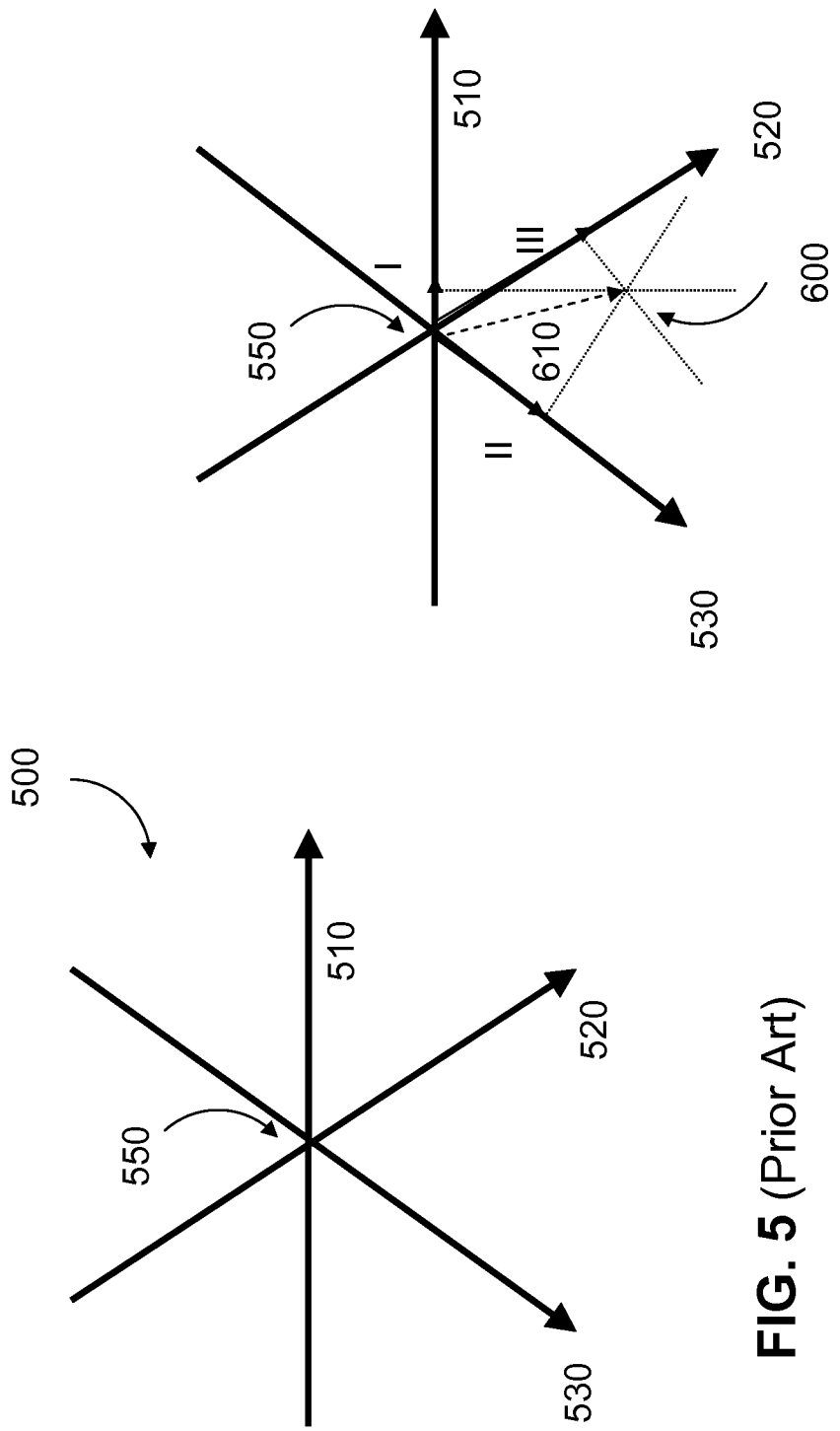
FIG. 5 is a vector diagram of a prior art coordinate system having three co-planar vector coordinate axes for representing bipolar surface ECG recordings.
FIG. 6 is a vector diagram of three sensing vectors, three normal lines (shown as dotted lines), and a resultant mean cardiac vector (shown as a dashed line) superimposed on the coordinate system shown in FIG. 5.

Referring to FIGS. 5 and 6, a mean cardiac vector 610 may be determined by finding the resultant electrical conduction vector (i.e., the vector sum) of at least two of the surface ECG lead signals I, II, and III at an instant in time at which at least one of the ECG signals is at an absolute maximum. In FIG. 5, a coordinate system 500 is presented in which three co-planar axes 510, 520, and 530 are used to represent bipolar surface ECG recordings in accordance with established conventions that place lead I at 0 degrees, lead II at 120 degrees, and lead III at 60 degrees. The center of coordinate system 500 is represented by a crossing point 550. In FIG. 6 the three signal vectors I, II, and III are plotted on coordinate system 500 at the same time for example, at a time coinciding with the peak of the QRS complex, so as to maximize the signal amplitudes. Signal amplitudes I, II, and III are represented by the lengths of the arrows from the crossing point 550 along axes 510, 520, and 530, respectively If a normal line is extended from the tip of each signal vector, the normal crossing point 600 specifies the tip of the resultant mean cardiac vector 610, the length and direction of which is represented by a dashed arrow in FIG. 6. Mean cardiac vector 610 then represents the direction of electrical activity in the heart at its maximum amplitude.

Figure 7:
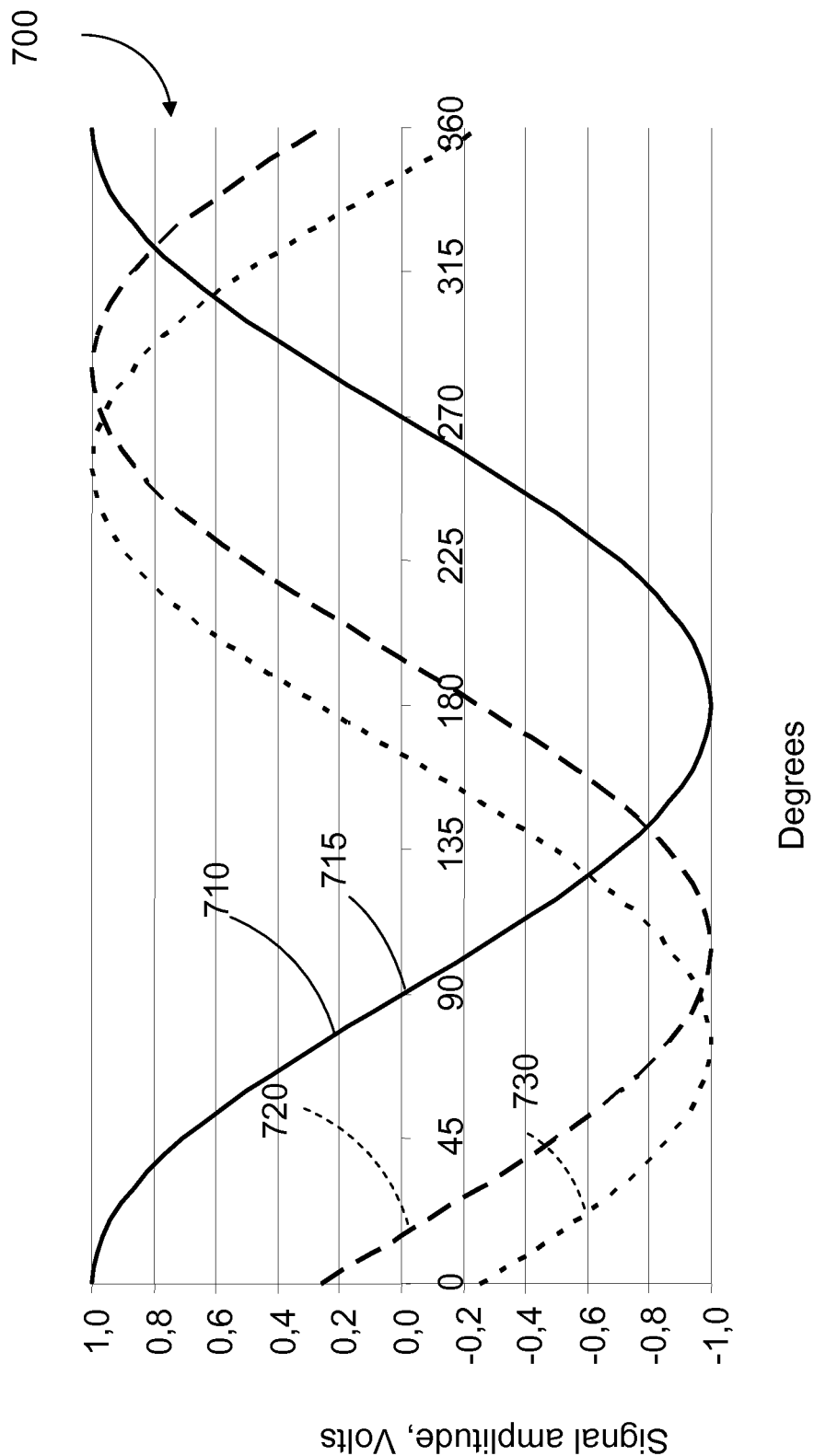
FIG. 7 is a graph of signal amplitudes recorded using the preferred configuration for subcutaneous electrode placement shown in FIG. 3.
Figure 8:
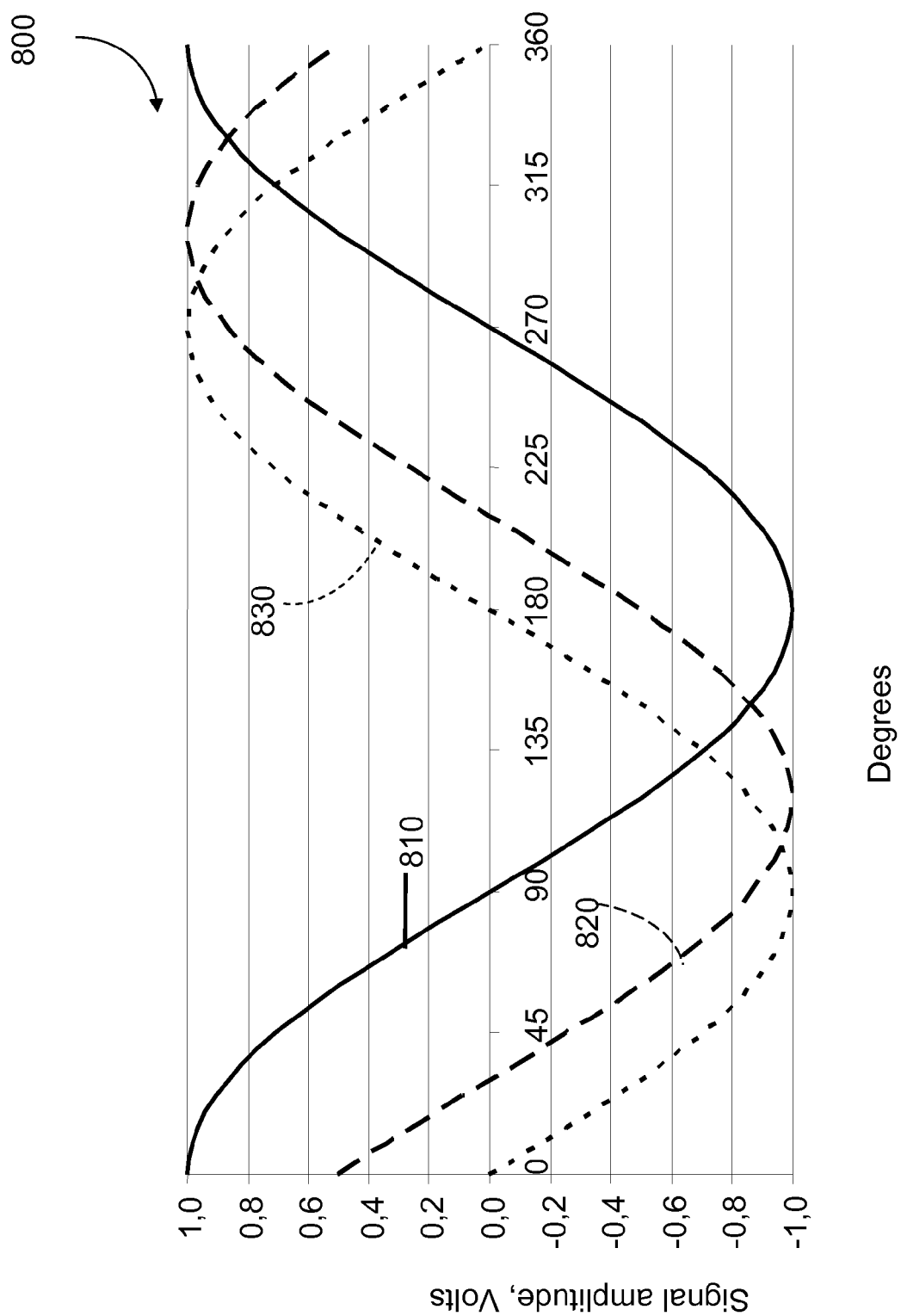
FIG. 8 is a graph of signal amplitudes and their vector sum, recorded using the preferred configuration for subcutaneous electrode placement shown in FIG. 3.

It can be seen that the maximum amplitude of each signal vector A, B, and C is partly dependent upon its angular orientation with respect to the mean cardiac vector 610, and partly upon the distance from the IMD 100 to the heart. Electrode configuration 350 may be rotated relative to the heart, through a rotation angle between 0 and 360 degrees. FIG. 7 shows an amplitude relationship 700 for electrode configuration 350 in which, for this example, the orientation of the device is rotated through 360 degrees relative to mean cardiac vector 610. The amplitudes of signal vectors A, B, and C are recorded every 15 degrees to show the amplitude relationships. A plot 710 (solid line) of the signal amplitude of vector A crosses the abscissa at an intersection point 715 at 90 degrees. Plots 720 (dashed line) and 730 (dotted line) of the signal amplitudes of vectors B and C, respectively are shown relative to plot 710. FIG. 8 shows a similar amplitude relationship 800 between signal amplitudes 810, 820, and 830 of sensing vectors A, B, and C, respectively, for electrode configuration 400. The abscissa in FIGS. 7 and 8 represents the orientation of sensing vectors relative to cardiac vector 610 in degrees.

Figure 9:
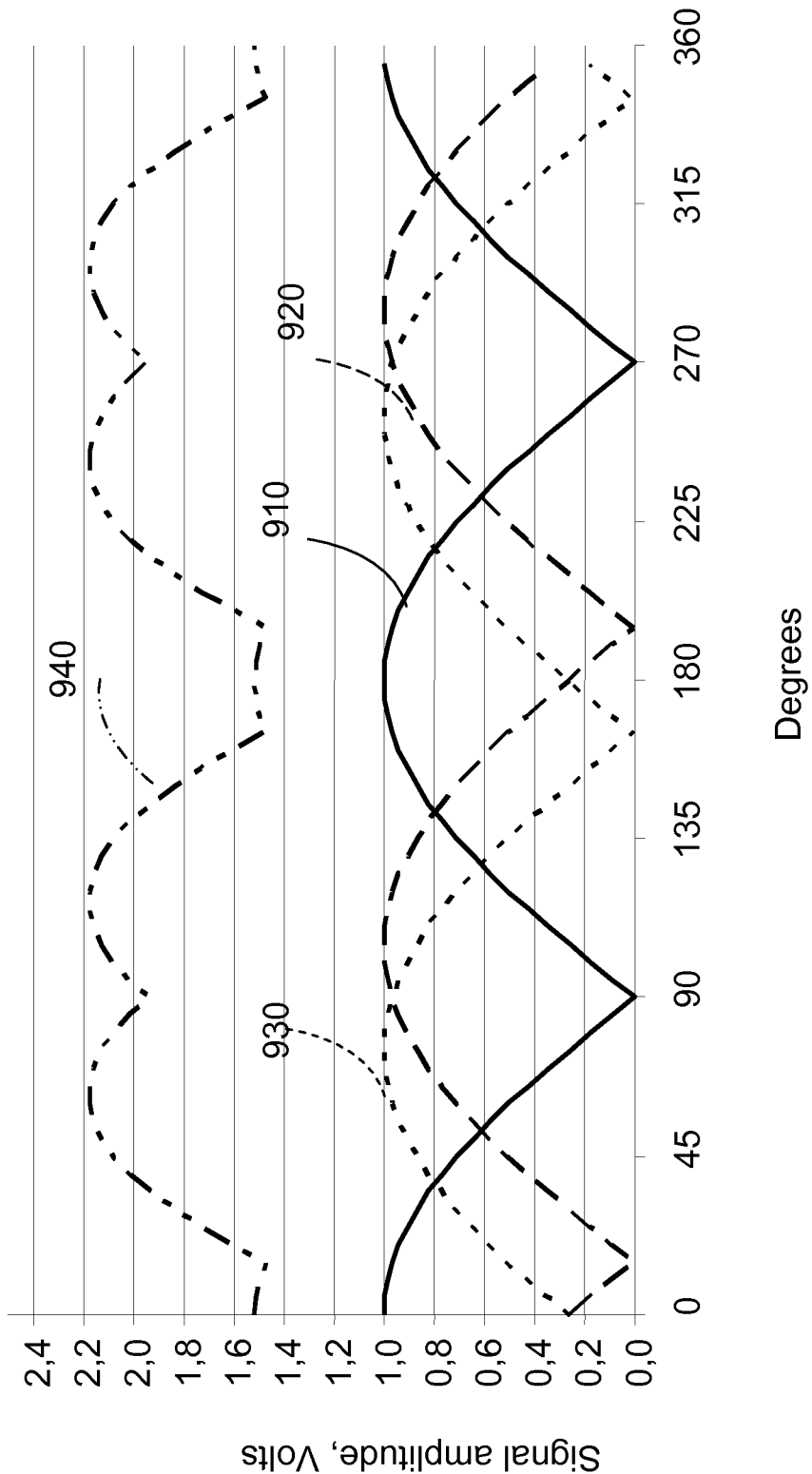
FIG. 9 is a graph of signal amplitudes recorded using the alternate configuration for subcutaneous electrode placement shown in FIG. 4.
Figure 10:
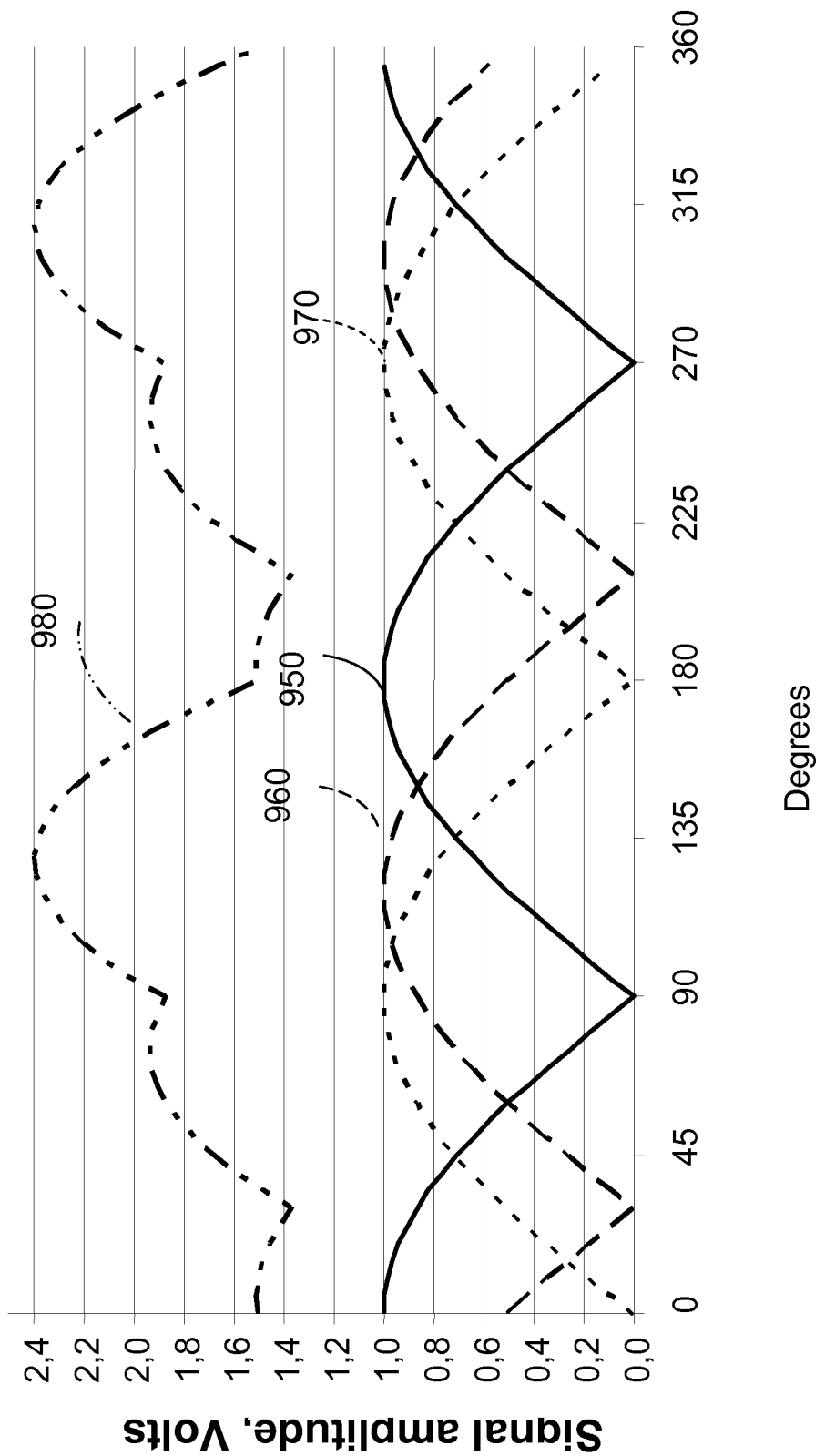
FIG. 10 is a graph of signal amplitudes and their vector sum, recorded using the alternate configuration for subcutaneous electrode placement shown in FIG. 4.

An exemplary optimal orientation of IMD 100 relative to the mean cardiac vector 610 may be determined relative to mean cardiac vector 610 for which the sum of the absolute values exceeds a predetermined threshold. This is shown in FIG. 9 for electrode configuration 350 and in FIG. 10 for electrode configuration 400. Plots 910, 920, and 930 of normalized signal amplitudes, equal to the absolute values of signal amplitudes 710, 720, and 730 of vectors A, B, and C are shown against a plot 940 showing the sum (dashed-dotted line) of normalized amplitudes 910, 920, and 930. Similarly, in FIG. 10, plots 950, 960, and 970 of normalized signal amplitudes, equal to the absolute values of signal amplitudes 810, 820, and 830 of sensing vectors A, B, and C are shown against a plot 980 showing the sum (dashed-dotted line) of normalized amplitudes 950, 960, and 970.

Figure 11:
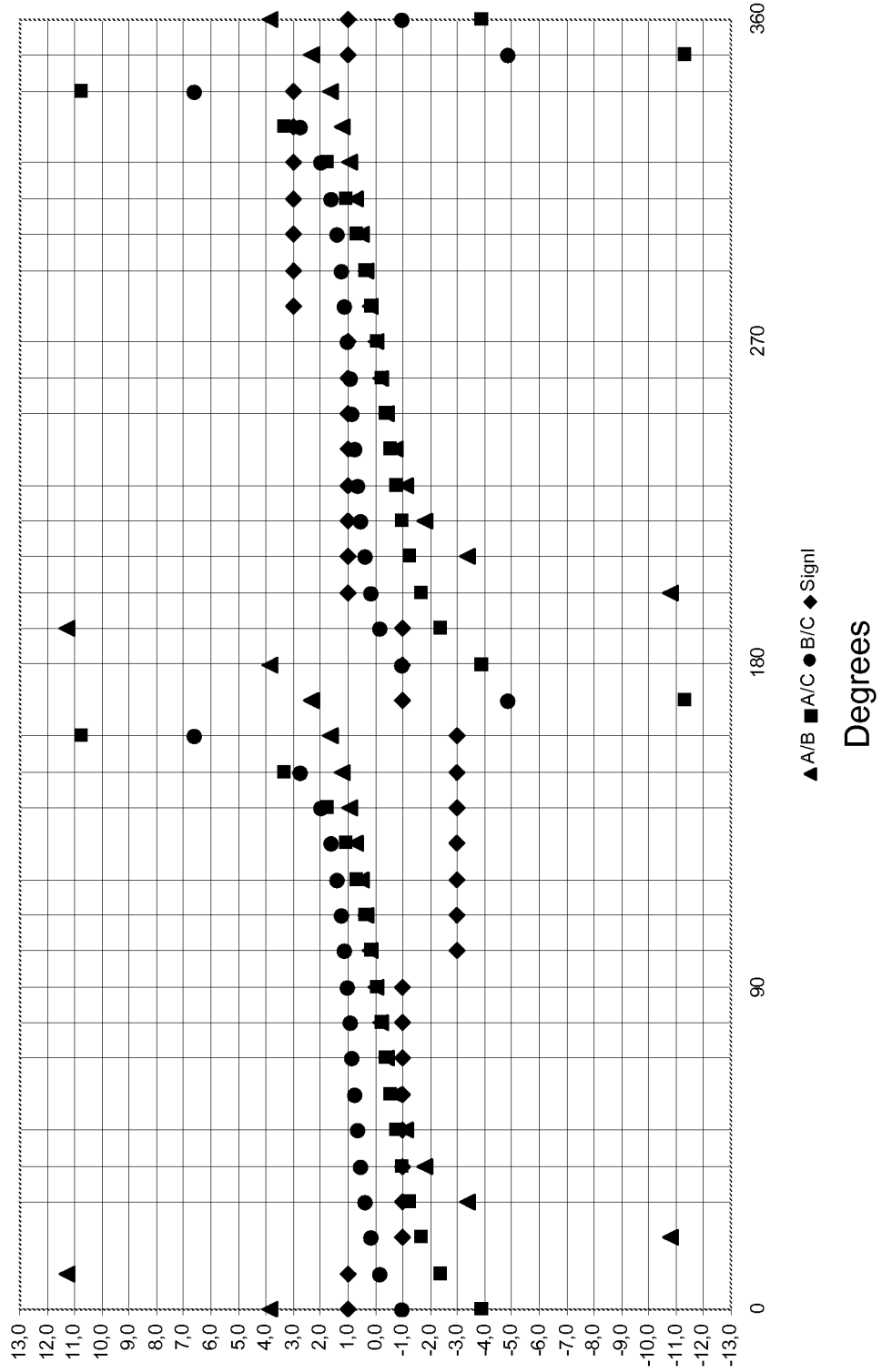
FIG. 11 is a plot of amplitude ratios and a sign indicator for signals recorded using the preferred configuration for subcutaneous electrode placement shown in FIG. 3.

After implantation, the orientation of IMD 100 relative to the mean cardiac vector 610 may be determined by evaluating amplitude ratios of the sensing vectors. To determine the orientation of the device, a clean QRS waveform from each channel is required. This may be obtained by averaging QRS signals over a time interval, for example, ten seconds, to reduce inherent noise. FIG. 11 shows a plot of amplitude ratios for electrode configuration 350, in which the abscissa represents the orientation in degrees of vector A relative to the cardiac vector 610. Plotted are the ratios A/B as triangles, the ratio B/C as quadrates and the ratio B/C as circles in steps of 10 degrees. Whereas the signal amplitudes of sensing vectors A, B, and C vary with both the orientation relative to, and the distance away from, the heart, the signal amplitude ratios of the vectors depend only on the orientation of the device relative to the mean cardiac vector 610.

Alternatively, an orientation data set may be derived from the ratio of A:B:C as a unique identifier of the orientation. In a preferred embodiment, processor 120 calculates amplitude ratios for the sensed vector signals, and may store the calculated amplitude ratios in the digital memory 130. Processor 120 may be programmed to verify whether the maximum amplitudes of sensing vectors A, B, and C occur at the same point in time and it may provide a corresponding indicator. It can be seen that a combination of the three amplitude ratios shown [A/B, A/C, B/C] is unique for each orientation of IMD 100 relative to the mean cardiac vector 610 over a range of 0 to 180 degrees.

If, in addition to the amplitude ratios, the signs of the sensing vectors are evaluated, a unique combination may be found for each orientation of IMD 100 relative to the mean cardiac vector 610. Processor 120 may be programmed to compute a sign indicator by converting the signs of the amplitudes of sensing vectors A, B, and C into integer values (positive sign equals 1, negative sign equals −1 and 0 otherwise) and then summing these integer values. Exemplary sign indicators are denoted as SignI in FIG. 11 and plotted as rhombuses. Sign indicator SignI may be stored in digital memory 130 as part of an orientation data set representing a particular orientation of IMD 100 relative to the mean cardiac vector 610. Elements of the orientation data set include the corresponding three amplitude ratios [A/B, A/C, B/C] and the sign indicator SignI, all of which are preferably recorded at substantially the same time.

Figure 12:
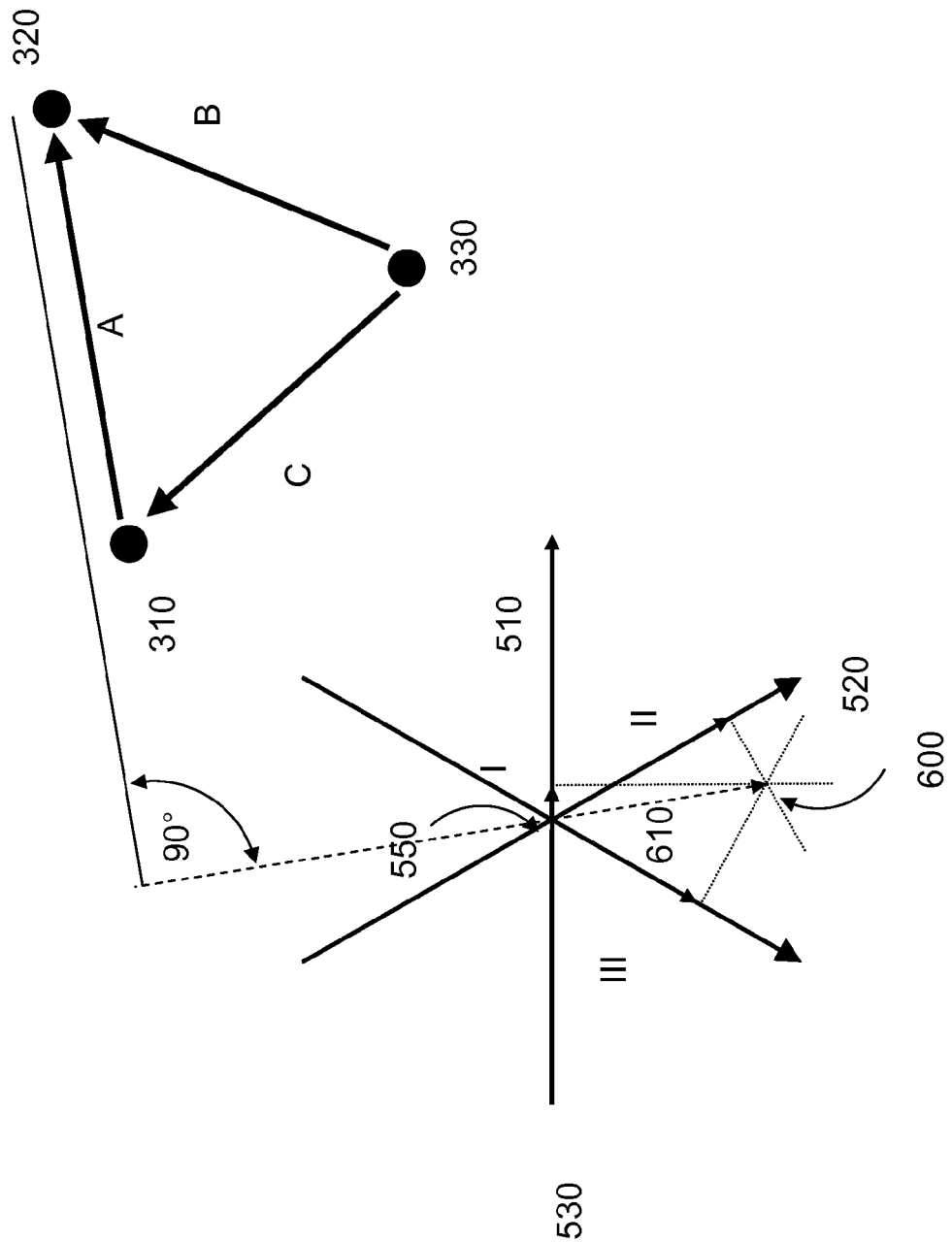
FIG. 12 is a diagram showing an orientation of the IMD rotated 90 degrees relative to the mean cardiac vector.

It is also possible to detect changes in the orientation of IMD 100, for example, to determine the cause of sensing amplitude degradation. In this case, a known orientation data set recorded at a first point in time is stored as a reference. For example, in the event of gross changes in an SECG, a new comparison may be performed to determine if IMD 100 changed position relative to the mean cardiac vector 610 (see FIG. 12). This comparison does not rely on any external devices and thus it can be performed remotely. For example, as the orientations of the vectors A, B and C relative to each other are determined by electrode orientation, expected vector ratios and sign indicators may be calculated for different orientations and stored as reference orientation data sets. Alternatively, IMD 100 may be placed in a fluid that simulates body fluid, (e.g., in a water bath), and vector ratios and a sign indicator for different orientations relative to a known signal vector representing the peak mean cardiac vector 610 may be recorded and stored as reference orientation data sets. A determination of the orientation of IMD 100 relative to the mean cardiac vector 610 may then be performed by comparing actual orientation data sets with the stored reference orientation data sets. Such a comparison may be accomplished in various ways, e.g., by storing reference orientation data sets as a look-up table and seeking in a preferred embodiment, a one-to-one identical match, or, in an alternative embodiment, a closest match of the orientation data set elements within a prescribed range.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may be evident within the true scope of this invention.

What is claimed is:

1. An implantable medical device (IMD), comprising:
    a hermetically sealed, biocompatible housing;
    at least three electrodes having fixed relative spacing, the electrodes being capable of subcutaneous detection of electrical signals;
    a power supply installed within the housing;
    electronic components installed within the housing and energized by the power supply, including:
        signal conditioning components, wherein each signal conditioning component is connected between a pair of electrodes to sense amplitudes of electrical activity, so as to form a set of at least three sensing vectors;
        a digital memory;
        a processor in communication with the digital memory and the signal conditioning components, the processor implemented to receive sensing vectors, compute amplitude ratios between different sensing vectors, and store in the digital memory the amplitude ratios corresponding to at least one orientation of the IMD.

2. The device of claim 1, in which the processor is further implemented to determine an orientation of the IMD by comparing the computed amplitude ratios to previously stored amplitude ratios.

3. The device of claim 1, wherein the electrical signals are cardiac signals, including a QRS complex signal and amplitude ratios are determined at a time coincident with an occurrence of the QRS complex signal.

4. The device of claim 1, further comprising a telemetry unit, wherein the telemetry unit transmits one or more of the amplitudes, amplitude ratios, and the determined orientation.

5. The device of claim 1, wherein the processor is further implemented to compute a sign indicator for the amplitudes and wherein the sign indicator is retained in the digital memory for at least one orientation of the device.

6. The device of claim 5, wherein the processor is further implemented to determine an orientation of the device by comparing the computed sign indicator to previously stored sign indicators, and wherein the determined orientation is retained in the digital memory.

7. The device of claim 6, further including a telemetry unit configured to transmit one or more of the amplitudes, amplitude ratios, sign indicator, and the determined orientation.

8. The device of claim 1 further comprising a remote device configured to receive a device orientation computed from the amplitude ratios, and compare different orientations to determine a change in orientation of the IMD.

9. A system, comprising:
   an implantable medical device (IMD), comprising:
      at least three subcutaneous electrodes having fixed relative spacing, for detecting electrical signals;
      a hermetically sealed, biocompatible housing;
      a power supply installed within the housing;
      electronic components installed within the housing and energized by the power supply, including:
         signal conditioning components, wherein each signal conditioning component is connected between a pair of electrodes for sensing amplitudes of electrical activity so as to form a set of at least three sensing vectors;
         a digital memory;
         a processor connected to the digital memory and the signal conditioning components, the processor being implemented to receive data from the signal conditioning components, compute amplitude ratios corresponding to each of the sensing vectors, and store in the digital memory the amplitude ratios corresponding to at least one orientation of the IMD, and determine an orientation of the IMD, by comparing the computed amplitude ratios to the stored amplitude ratios; and
         a telemetry unit, connected to the processor, for transmitting the orientation; and
   a remote device, for receiving the transmitted orientation, storing the orientation in the digital memory, and comparing different stored orientations to determine a change in orientation of the IMD.

10. The system of claim 9, wherein the electrical signals are cardiac signals, including a QRS complex signal and amplitude ratios are determined at a time coincident with an occurrence of the QRS complex signal.

11. The system of claim 9, wherein the processor is further implemented to compute a sign indicator for the amplitudes and wherein the sign indicator is retained in the digital memory for at least one orientation of the device.

12. The system of claim 11, wherein the processor is further implemented to determine an orientation of the device by comparing the computed sign indicator to previously stored sign indicators, and wherein the determined orientation is retained in the digital memory.

13. A method of determining an orientation for an implanted medical device (IMD), comprising:
   detecting at least three electrical signals;
   conditioning the electrical signals so as to form a set of at least three sensing vectors;
   computing amplitude ratios corresponding to each of the sensing vectors;
   storing the amplitude ratios corresponding to at least one orientation of the IMD; and
   determining the orientation of the IMD by comparing the computed amplitude ratios to the stored amplitude ratios.

14. The method of claim 13 further including the steps of:
   a. computing a sign indicator for each sensing vector, and
   b. retaining one or more of the sign indicators in a memory for at least one orientation of the IMD.

15. The method of claim 14 further including the steps of:
   a. determining an orientation of the IMD from the sign indicators, and
   b. retaining the determined orientation in the digital memory.

16. The method of claim 13 wherein:
   a. the detected electrical signals are cardiac signals, the cardiac signals each including a QRS complex signal; and
   b. the amplitude ratios are computed over times coincident with the QRS complex signals.

17. An implantable medical device (IMD) including:
   a. at least three spaced electrodes configured to detect electrical activity within a living body, and
   b. a telemetry unit configured to transmit information from the IMD,
   wherein the IMD is configured to:
   (1) sense at least three sensing vectors, each sensing vector representing an electrical activity amplitude between a respective pair of the electrodes;
   (2) determine at least three amplitude ratios, each amplitude ratio being determined between a respective pair of the sensing vectors; and
   (3) transmit from the IMD at least one of:
      (a) the amplitude ratios, and
      (b) an orientation of the IMD determined from the amplitude ratios.

18. The device of claim 17 wherein the IMD is further configured to:
   a. store amplitude ratios over time, and
   b. determine orientation changes of the IMD over time from the stored amplitude ratios.

19. The device of claim 17 wherein:
   a. the IMD is further configured to compute a sign indicator for each sensing vector, and
   b. one or more of the sign indicators is retained in the digital memory for at least one orientation of the device.

20. The device of claim 19 wherein:
   a. the IMD is further configured to compare each computed sign indicator to a previously stored sign indicator, thereby determining an orientation of the device, and
   b. the determined orientation is retained in the digital memory.

* * * * *